US010281203B2

(12) United States Patent
Guillard et al.

(10) Patent No.: US 10,281,203 B2
(45) Date of Patent: May 7, 2019

(54) METHOD FOR LIQUEFACTION OF INDUSTRIAL GAS BY INTEGRATION OF METHANOL PLANT AND AIR SEPARATION UNIT (71) Applicant: L'Air Liquide, Societe Anonyme pour l'Etude et l'Exploitation des Procedes Georges Claude, Paris (FR)

(72) Inventors: Alain Guillard, Houston, TX (US); Michael A. Turney, Houston, TX (US); Alexander Roesch, Katy, TX (US)

(73) Assignee: L'Air Liquide Societe Anonyme Pour L'Etude Et L'Exploitation Des Procedes Georges Claude, Paris (FR)

( * ) Notice: Subject to any disclaimer, the term of this patent is extended or adjusted under 35 U.S.C. 154(b) by 118 days.

(21) Appl. No.: 15/414,142

(22) Filed: Jan. 24, 2017

(65) Prior Publication Data
US 2018/0038644 A1 Feb. 8, 2018

Related U.S. Application Data
(60) Provisional application No. 62/371,497, filed on Aug. 5, 2016.

(51) Int. Cl.
F25J 1/00 (2006.01)
F25J 1/02 (2006.01)
(Continued)

(52) U.S. Cl.
CPC ............. *F25J 1/0234* (2013.01); *C01B 3/56* (2013.01); *C07C 29/1518* (2013.01);
(Continued)

(58) Field of Classification Search
CPC .. F25J 1/00; F25J 1/0022; F25J 1/0032; F25J 1/0035; F25J 1/0037; F25J 1/004;
(Continued)

(56) References Cited

U.S. PATENT DOCUMENTS 2,983,585 A   5/1961   Smith
3,347,055 A   10/1967  Blanchard et al.
(Continued)

FOREIGN PATENT DOCUMENTS

CN   103 017 480   4/2013
CN   204 063 780   12/2014
(Continued)

OTHER PUBLICATIONS

Quack, "Conceptual Design of a High Efficiency Large Capacity Hydrogen Liquefier," Adv. Cryog. Eng., Proc. CEC, Madison 2001, AIP, vol. 613, 255-263—Abstract Only.
(Continued)

Primary Examiner — Frantz F Jules
Assistant Examiner — Erik Mendoza-Wilkenfel
(74) Attorney, Agent, or Firm — Justin K. Murray (57) ABSTRACT A method for the liquefaction of an industrial gas by integration of a methanol plant and an air separation unit (ASU) is provided. The method can include the steps of: (a) providing a pressurized natural gas stream, a pressurized purge gas stream composed predominately of hydrogen and originating from a methanol plant, and a pressurized air gas stream comprising an air gas from the ASU; (b) expanding three different pressurized gases to produce three cooled streams, wherein the three different pressurized gases consist of the pressurized natural gas stream, the pressurized purge gas stream, and the pressurized air gas stream; and (c) liquefying the industrial gas in a liquefaction unit against the three cooled streams to produce a liquefied industrial gas stream, wherein the industrial gas to be liquefied is selected from the group consisting of a first portion of the pressurized natural gas stream, a nitrogen gas stream, hydrogen and combinations thereof.

19 Claims, 5 Drawing Sheets (51) Int. Cl.
*F25J 3/04* (2006.01)
*C07C 29/151* (2006.01)
*C01B 3/56* (2006.01)
*C10L 3/10* (2006.01)

(52) U.S. Cl.
CPC ............ *C10L 3/103* (2013.01); *F25J 1/0022* (2013.01); *F25J 1/0037* (2013.01); *F25J 1/0067* (2013.01); *F25J 1/0072* (2013.01); *F25J 1/023* (2013.01); *F25J 1/0221* (2013.01); *F25J 1/0227* (2013.01); *F25J 1/0229* (2013.01); *F25J 1/0232* (2013.01); *F25J 1/0297* (2013.01); *F25J 3/046* (2013.01); *F25J 3/04018* (2013.01); *F25J 3/04024* (2013.01); *F25J 3/04121* (2013.01); *F25J 3/04412* (2013.01); *F25J 3/04563* (2013.01); *F25J 3/04593* (2013.01); *C01B 2203/042* (2013.01); *C01B 2203/061* (2013.01); *F25J 1/00* (2013.01); *F25J 2200/06* (2013.01); *F25J 2210/06* (2013.01); *F25J 2210/12* (2013.01); *F25J 2210/40* (2013.01); *F25J 2210/42* (2013.01); *F25J 2210/60* (2013.01); *F25J 2215/40* (2013.01); *F25J 2220/64* (2013.01); *F25J 2220/66* (2013.01); *F25J 2220/68* (2013.01); *F25J 2230/20* (2013.01); *F25J 2230/30* (2013.01); *F25J 2230/40* (2013.01); *F25J 2230/42* (2013.01); *F25J 2240/02* (2013.01); *F25J 2245/40* (2013.01); *F25J 2245/42* (2013.01); *F25J 2260/44* (2013.01); *F25J 2270/04* (2013.01); *F25J 2270/14* (2013.01); *F25J 2270/16* (2013.01); *F25J 2290/12* (2013.01); *F25J 2290/60* (2013.01)

(58) Field of Classification Search
CPC .......... F25J 1/023; F25J 1/0235; F25J 1/0236; F25J 1/0237; F25J 1/0232; F25J 1/0234; F25J 1/0238; F25J 1/0239; F25J 1/0241; F25J 1/0264; F25J 1/0267; F25J 3/0252; F25J 3/0204; F25J 3/0223; F25J 3/0271; F25J 2215/60; F25J 2220/02; F25J 2220/40; F25J 2220/66; F25J 2220/68; F25J 2220/80; F25J 3/0257; F25J 3/04018; F25J 3/0403; F25J 3/04054; F25J 3/0406; C01B 2203/042; C01B 2203/061; C01B 3/56; C01B 3/103; C07C 29/1518
See application file for complete search history.

(56) References Cited

U.S. PATENT DOCUMENTS

| | | | |
|---|---|---|---|
| 3,380,809 A | | 4/1968 | Newton |
| 3,446,747 A | | 5/1969 | Bongiorno |
| 3,501,516 A | * | 3/1970 | Parrish ...................... C01B 3/38 252/373 |
| 3,929,438 A | | 12/1975 | Harper et al. |
| 4,185,456 A | * | 1/1980 | Cummings ................ F02C 3/24 252/373 |
| 4,867,773 A | * | 9/1989 | Thorogood .......... F25J 3/04284 62/652 |
| 5,231,835 A | | 8/1993 | Beddome et al. |
| 6,131,407 A | | 10/2000 | Wissolik |
| 6,196,021 B1 | | 3/2001 | Wissolik |
| 6,412,302 B1 | | 7/2002 | Foglietta |
| 6,484,533 B1 | | 11/2002 | Allam et al. |
| 6,694,774 B1 | | 2/2004 | Rashad et al. |
| 7,559,213 B2 | | 7/2009 | Allam et al. |
| 2003/0032844 A1 | * | 2/2003 | Seiki .................. C07C 29/1518 568/700 |
| 2003/0191196 A1 | | 10/2003 | Madhubhai et al. |
| 2003/0226373 A1 | * | 12/2003 | Prible ..................... B63B 27/24 62/612 |
| 2004/0083756 A1 | * | 5/2004 | Tranier .................. F25J 1/0022 62/614 |
| 2005/0020434 A1 | | 1/2005 | Ansorge et al. |
| 2006/0260321 A1 | | 11/2006 | Minkkinen et al. |
| 2007/0107465 A1 | * | 5/2007 | Turner ................... F25J 1/0022 62/613 |
| 2007/0225384 A1 | * | 9/2007 | Thiebaut ................. C01B 3/025 518/705 |
| 2008/0087863 A1 | | 4/2008 | Fisciier et al. |
| 2009/0090131 A1 | * | 4/2009 | Kuo ......................... F28D 5/00 62/614 |
| 2009/0120127 A1 | * | 5/2009 | Dragomir .............. F25J 1/0022 62/613 |
| 2010/0047160 A1 | * | 2/2010 | Allam ..................... C01B 3/382 423/651 |
| 2010/0126215 A1 | * | 5/2010 | Court ..................... F25J 1/0022 62/617 |
| 2010/0150810 A1 | * | 6/2010 | Yoshida ................. B01J 8/0411 423/359 |
| 2010/0251763 A1 | * | 10/2010 | Audun .................... B63B 25/16 62/614 |
| 2011/0030332 A1 | * | 2/2011 | Vandor .................. F01D 15/005 60/39.83 |
| 2011/0301252 A1 | * | 12/2011 | Ostuni ................. C07C 29/1518 518/702 |
| 2012/0107227 A1 | | 5/2012 | Fischer et al. |
| 2012/0144837 A1 | | 6/2012 | Rasmussen et al. |
| 2012/0148472 A1 | * | 6/2012 | Ahmed .................. C01B 3/025 423/359 |
| 2013/0192297 A1 | * | 8/2013 | Mak ....................... F25J 1/0022 62/613 |
| 2014/0250911 A1 | * | 9/2014 | Huntington ............ F25J 1/0022 60/780 |
| 2014/0352353 A1 | | 12/2014 | Wissolik |
| 2015/0114035 A1 | * | 4/2015 | Briglia ..................... F25J 5/005 62/620 |
| 2015/0233290 A1 | | 8/2015 | Lee et al. |
| 2016/0216030 A1 | | 7/2016 | Truong et al. |
| 2017/0016668 A1 | * | 1/2017 | Pierre, Jr. ................. F25J 3/08 |

FOREIGN PATENT DOCUMENTS

| | | |
|---|---|---|
| JP | 2002 243360 A | 8/2002 |
| JP | 2004 210 597 | 7/2004 |
| WO | WO 00/57118 | 9/2000 |
| WO | WO 2004/065869 | 8/2004 |

OTHER PUBLICATIONS

International Search Report and Written Opinion for PCT/US2017/045524, dated Nov. 10, 2017.
International Search Report and Written Opinion for PCT/US2017/045537, dated Nov. 29, 2017.
International Search Report and Written Opinion for PCT/US2017/045544, dated Dec. 12, 2017.
International Search Report and Written Opinion for PCT/US2017/045549, dated Jan. 18, 2018.
International Search Report and Written Opinion for PCT/US2017/045555, dated Oct. 14, 2017.
Geijsel, J.I., et al, "Synergies Between LNG and Gas to Liquids Conversion," International Conference and Exhibition on Liquefied Natural Gas, Jan. 1, 2001.
Coulson, et al., "Carbon Capture Optionsfor LNG Liquefaction," 16th International Conference & Exhibition on Liquefied Natural Gas, pp. 1-17, Apr. 2010.
Syed, M.T., et al, "An Economic Analysis of Three Hydrogen Liquefaction Systems," Int. J. Hydrogen Energy, vol. 23, No. 7, pp. 565-576, 1998.
Bracha, M., et al, "Large-Scale Hydrogen Liquefaction in Germany," Int. J. Hydrogen Energy, vol. 19, No. 1, pp. 53-59, 1994.

(56) References Cited

OTHER PUBLICATIONS

Ballout, et al., "Comparison of Present Day Peakshaving Liquefaction Technologies," AICHE Spring Meeting, Natural Gas Utilization Conference, vol. 8, Apr. 2008, pp. 30-47.

* cited by examiner

METHOD FOR LIQUEFACTION OF INDUSTRIAL GAS BY INTEGRATION OF METHANOL PLANT AND AIR SEPARATION UNIT

CROSS REFERENCE TO RELATED APPLICATIONS

This application is a non-provisional application of U.S. Provisional Applicant No. 62/371,497, filed Aug. 5, 2016, which is herein incorporated by reference in its entirety.

TECHNICAL FIELD OF THE INVENTION

The present invention relates to an apparatus and method for liquefaction of an industrial gas stream, where examples of industrial gases are natural gas, nitrogen, methane, ethane, ethylene, and hydrogen. More specifically, embodiments of the present invention are related to liquefying an industrial gas stream by using a combination of refrigeration from pressure letdown of the natural gas, a purge stream originating from a methanol plant, and at least one stream originating from an air separation unit.

BACKGROUND OF THE INVENTION

A methanol plant requires large quantities of natural gas feed from a high pressure transmission network. A portion of this natural gas feed is reduced in pressure through a control valve to low pressure and burned as fuel in the Steam Methane Reformer (SMR), and/or fired heater, and/or gas turbine, auxiliary boiler, steam boiler, and auxiliary burners.

The remaining portion (and majority) of the natural gas feed is processed in desulfurization unit, and reacted in SMR and/or ATR (Autothermal Reformer) to produce a syngas. In a methanol plant the syngas is further compressed to approximately 50-150 bara and reacted to produce methanol and a pressurized byproduct stream that is hydrogen rich. This byproduct stream can be split into two fractions, with the first fraction going to a Pressure Swing Adsorber (PSA) to produce a purified hydrogen product, and the remaining second fraction, also referred to as a purge gas, is reduced in pressure with a control valve to approximately 0.3-7 bara and used as fuel within the methanol plant.

With respect to air separation units (ASU), oxygen and nitrogen are separated from atmospheric air by cryogenic distillation. The required separation energy is provided by a main air compressor (MAC). The oxygen (and possibly nitrogen) product compression is provided by pumping the cryogenic liquid and vaporizing at the required product pressure in the main ASU heat exchanger. The energy required for this product vaporization, as well as energy required for liquefied products, is provided by a booster air compressor (BAC).

SUMMARY OF THE INVENTION

As noted supra, the typical methanol process described above includes at least two streams: high pressure natural gas letdown to fuel and hydrogen rich purge as letdown as fuel, which do not utilize the high pressure energy available.

In certain embodiments, the potential high pressure energy of these two streams may be utilized by expansion of the two streams in conjunction with expansion of a third pressurized gas stream originating from an ASU for refrigeration purposes.

In one embodiment, at least a portion of the natural gas and the hydrogen rich purge streams are diverted to an exchanger where they are cooled down, then expanded in turbines to extract energy and produce colder process streams which are then re-warmed in the exchanger to cool the turbine inlet streams as well as the fluid to be liquefied (e.g. natural gas, ethane, methane, nitrogen, hydrogen, ethylene, etc. . . . ).

The third source of refrigeration can be provided by expansion of a pressurized gas stream originating from an ASU selected from the group consisting of air from the discharge of the main air compressor (MAC) following purification, nitrogen coming from the medium pressure column after warming in the ASU heat exchanger, and combinations thereof. Alternatively, the withdrawal location of the medium pressure air from the ASU may be partially cooled from the discharge of the ASU heat exchanger and/or the location of the nitrogen may be partially cooled from the inlet of ASU heat exchanger.

During operation of an ASU, it is typical for the MAC to be operating at below its maximum design condition. This is because the maximum design conditions are often based on worst case conditions (e.g., maximum liquid products, maximum high pressure gaseous oxygen, summer conditions, etc. . . . ), which may be occasionally required but are rarely an actual operating point. Additionally, the design capacities of the major equipment such as MAC and BAC can be maximized to the limit of a step change in capital cost, for example based on the limit of a compressor frame size.

Additionally, in some cases, the MAC can be used to provide additional air to the front end purification unit during the repressurization step of the regeneration cycle. As the repressurization step only occurs for a small portion of the overall purification cycle of the front end purification unit, the MAC is operating at below maximum capacity for the majority of the time. Therefore, in a typical air separation unit, there is often excess capacity available from the MAC and pretreatment such that high pressure air can be withdrawn from the ASU at approximately 4-40 bara with some operating cost but with little or zero additional capital cost.

Therefore, certain embodiments of the invention provide for an improved process for liquefaction of an industrial gaseous stream, for example natural gas, that incorporates the available wasted energy of these two processes in an efficient manner.

In one embodiment, a method for the liquefaction of an industrial gas selected from the group consisting of natural gas, nitrogen, and combinations thereof, is provided. In one embodiment, the method can include the steps of: a) withdrawing a pressurized natural gas stream from a natural gas pipeline; b) removing carbon dioxide and water from the pressurized natural gas stream; c) expanding the pressurized natural gas stream to form an expanded natural gas stream and warming the expanded natural gas stream in a first portion of a heat exchanger against the industrial gas to form a warmed natural gas stream; d) sending the warmed natural gas stream to a methanol production facility under conditions effective for producing a methanol stream, a purified hydrogen stream, and a purge gas rich in hydrogen; e) expanding the purge gas rich in hydrogen to form an expanded purge gas and warming the expanded purge gas in a second portion of the heat exchanger against the industrial gas to form a warmed purge gas stream; f) sending the warmed purge gas stream to the methanol production facility for use as fuel; and g) expanding a pressurized air gas stream from or derived from an air separation unit (ASU) to form an expanded air gas stream and warming the expanded air gas stream in a third portion of the heat exchanger against the industrial gas to form a warmed air gas stream, wherein the industrial gas is liquefied during step g). In another embodiment, the industrial gas may be partially liquefied in steps c) and/or e).

In optional embodiments of the method for the liquefaction of the industrial gas:

the air gas from or derived from an ASU is a gas stream selected from the group consisting of compressed and purified air from a main air compressor, a nitrogen stream from a medium pressure column, and combinations thereof;

the industrial gas further comprises trace components having a freezing point temperature warmer than that of methane, wherein the first portion of the heat exchanger and the second portion of the heat exchanger are kept at temperatures warmer than the freezing point temperature of the trace components, and wherein the trace components are removed from the industrial gas prior to the industrial gas being cooled in the third portion of the heat exchanger; and/or the third portion of cooling is provided at colder temperatures than both the first portion of cooling and the second portion of cooling.

In another embodiment, the method for the liquefaction of the industrial gas can include the steps of: (a) providing a pressurized natural gas stream, a pressurized purge gas stream originating from a methanol plant, and a pressurized air gas stream comprising an air gas from an air separation unit (ASU), wherein the pressurized purge gas stream is comprised predominately of hydrogen, wherein the pressurized air gas stream has an oxygen concentration at or below that of atmospheric air; (b) expanding three different pressurized gases to produce three cooled streams, wherein the three different pressurized gases consist of the pressurized natural gas stream, the pressurized purge gas stream, and the pressurized air gas stream; and (c) liquefying the industrial gas in a liquefaction unit against the three cooled streams to produce a liquefied industrial gas stream, wherein the industrial gas to be liquefied is selected from the group consisting of a first portion of the pressurized natural gas stream, a nitrogen gas stream from a nitrogen pipeline, and combinations thereof.

In optional embodiments of the method for the liquefaction of the industrial gas:

the air gas from an ASU is a gas stream selected from the group consisting of compressed and purified air from a main air compressor, a nitrogen stream originating from a medium pressure column of the ASU, and combinations thereof, wherein the air gas from the ASU is at a pressure between 4 and 40 bara;

the pressurized natural gas stream comprises methane and trace components, wherein the trace components have freezing point temperatures warmer than that of methane;

the trace components have a freezing point temperature warmer than about 140° C.;

in steps (b) and (c): the pressurized natural gas stream provides a first portion of cooling to the industrial gas, the pressurized purge gas stream provides a second portion of cooling to the industrial gas, and the pressurized air gas stream provides a third portion of cooling to the industrial gas, wherein the third portion of the cooling is at a temperature that is colder than the first portion of the cooling and the second portion of the cooling;

the pressurized air gas stream further comprises nitrogen gas from a nitrogen pipeline;

at least a portion of the air gas of the pressurized air gas stream is withdrawn at a location downstream a main air compressor (MAC) of the ASU at or slightly below an outlet pressure of the MAC;

the flow of the air gas of the pressurized air gas stream withdrawn from the outlet of the MAC and provided in step (a) is only withdrawn during periods wherein there is no repressurization step taking place within a front end purification unit of the ASU;

the flow of the air gas of the pressurized air gas stream withdrawn from the outlet of the MAC and provided in step (a) accounts for less than about 20% of the total volumetric flow of air coming from the outlet of the MAC, and more preferably accounts for less than about 5% of the total volumetric flow of air coming from the outlet of the MAC; and/or the three different expansions in step (b) are performed in at least three separate turbines.

In another embodiment, the method for the liquefaction of the industrial gas can include the steps of: a) withdrawing a pressurized natural gas stream from a natural gas pipeline; b) sending a first portion of the pressurized natural gas stream to a methanol production facility under conditions effective for producing a methanol stream, a purified hydrogen stream, and a purge gas rich in hydrogen; c) providing a first portion of cooling by expanding a second portion of the pressurized natural gas stream; d) providing a second portion of cooling by expanding the purge gas rich in hydrogen from step b); e) providing a third portion of cooling by expanding a first portion of a pressurized air gas stream from or derived from an air separation unit (ASU), wherein the air gas from or derived from an ASU is a gas stream selected from the group consisting of compressed and purified air from a main air compressor, a nitrogen stream from a medium pressure column, and combinations thereof; f) cooling the industrial gas in a heat exchanger using the first portion of cooling and the second portion of cooling; and g) further cooling and liquefying the industrial gas in the heat exchanger using the third portion of cooling to produce a liquefied industrial gas.

In optional embodiments of the method for the liquefaction of the industrial gas:

the third portion of cooling is provided at colder temperatures than both the first portion of cooling and the second portion of cooling;

the third portion of the pressurized natural gas stream is cooled to a temperature warmer than about −140° C. in step f); and/or the third portion of the pressurized natural gas stream is cooled to a temperature between −140° C. to −165° C. in step g).

BRIEF DESCRIPTION OF THE DRAWINGS

These and other features, aspects, and advantages of the present invention will become better understood with regard to the following description, claims, and accompanying drawings. It is to be noted, however, that the drawings illustrate only several embodiments of the invention and are therefore not to be considered limiting of the invention's scope as it can admit to other equally effective embodiments.

DETAILED DESCRIPTION

While the invention will be described in connection with several embodiments, it will be understood that it is not intended to limit the invention to those embodiments. On the contrary, it is intended to cover all the alternatives, modifications and equivalence as may be included within the spirit and scope of the invention defined by the appended claims.

In one embodiment, it is proposed to utilize the potential high pressure energy of the two streams in the above-described methanol process: 1) high pressure natural gas letdown to fuel and 2) high pressure hydrogen rich purge gas letdown as fuel. At least a portion of these streams can be diverted to an exchanger where they can be cooled down, then expanded in a turbine to extract energy and produce a colder process stream, which is then re-warmed in the exchanger to cool the turbine inlet streams, as well as the fluid to be liquefied (e.g., natural gas for LNG or nitrogen for LIN). For a chosen turbine discharge temperature, the turbine inlet temperature can be a result of the available pressure ratio across the turbine. Therefore, in certain embodiments, the two diverted streams from the methanol process are not cooled down prior to expansion.

Because the natural gas stream and purge gas streams can contain some trace components such as, but not limited to ethane, propane, and butane+, there is a low temperature limit for the turbine discharge to prevent liquid formation, which creates process complexities at low levels and turbine damage at high levels. In certain embodiments, this temperature limit can be in the range of −100° C. depending on composition and pressure. For purposes herein, about −100° C. includes −100° C.+/−30° C. Those of ordinary skill in the art will recognize that this lower level temperature limit for the natural gas stream is preferably selected to prevent adverse process conditions (e.g., excess liquid production) coming out of the turbine discharge. In one embodiment, the molar fraction of liquid at the turbine discharge is less than 20%, preferably less than 15%, more preferably less than 10%. In one embodiment, no liquid production is preferred in the discharge of the turbines.

The liquefaction temperature of low pressure natural gas is approximately −160° C.; therefore, an additional refrigerant is included in embodiments of the present invention in order to liquefy the natural gas at temperatures below the lower limit of the natural gas stream. In one embodiment, the additional refrigerant provides refrigeration in the temperature range from about −100° C. to −160° C. In one embodiment, this additional refrigeration can be provided by expansion of nitrogen and/or air from the ASU. As such, the additional refrigeration can be provided by a stream originating from an ASU and/or from a gas stream derived from an ASU (e.g., nitrogen from a pipeline being a gas stream derived from an ASU).

Oxygen and nitrogen are separated from atmospheric air by cryogenic distillation. The required separation energy is provided by a main air compressor (MAC). Air at approximately 6 bara from the MAC is purified to remove $H_2O$ and $CO_2$ for cryogenic processing in the medium pressure (MP) column (sometimes also referred to as higher pressure (HP) column). The air flows upward in the MP column as it is enriched in nitrogen and is then condensed by heat exchange against vaporizing liquid oxygen in the LP column. At least a portion of this condensed nitrogen provides the reflux needed for the medium pressure (MP) distillation column. During operation of a typical double column, a portion of the pure nitrogen stream can be withdrawn from the MP column and sent to the top of the lower pressure (LP) column to provide reflux for the LP column. These nitrogen rich reflux streams for the MP and LP columns are used to separate the oxygen from nitrogen or "wash down" the oxygen. This reflux is often in excess of what is required for efficient distillation. For example, a portion of the nitrogen at the top of the MP column can be removed as product without significantly reducing the distillation recoveries (>99% O2 recovery can still be achieved).

This product nitrogen, which has been removed from the MP column, is often valorized by injecting at an intermediate stage of a nitrogen product compressor in order to reduce the nitrogen compression energy compared to a nitrogen compressor with only a low pressure feed.

For air separation plants where this potential for medium pressure $N_2$ is not valorized as described above, there is an opportunity to utilize this medium pressure nitrogen compression energy directly in an external liquefier.

As described above, the pressurized air from the MAC of the ASU can be available at approximately the operating pressures of the MP column (e.g., 4 to 7 bara) and at relatively low cost due to the typical operating range of the ASU and worst case equipment design basis. Moreover, with integration of the methanol plant, additional savings can be achieved by driving the MAC and BAC using steam turbines with available steam from the methanol plant. In certain embodiments, the MAC and purification unit operate at higher pressures (10 to 40 bara) such that refrigeration for the ASU is provided by pressure letdown through a turbine to the MP column operating at 4-7 bara.

In another embodiment, a portion of the high pressure air that is not sent to the ASU cold box can be mixed with available medium pressure nitrogen ($MPN_2$) from the MP column if the $MPN_2$ is not being valorized in the nitrogen compressor. This can result in a low-cost, lean synthetic medium pressure air (or impure $N_2$) stream in the range of 4-7 bara to be available for expansion refrigeration in the liquefier. In one embodiment, the air injection may be limited by the combustibility limit of $O_2$ in methane (approx 12%) or $O_2$ in $H_2$ (approx 6%) or by design margin to these limits if there is potential leak.

Figure 1:
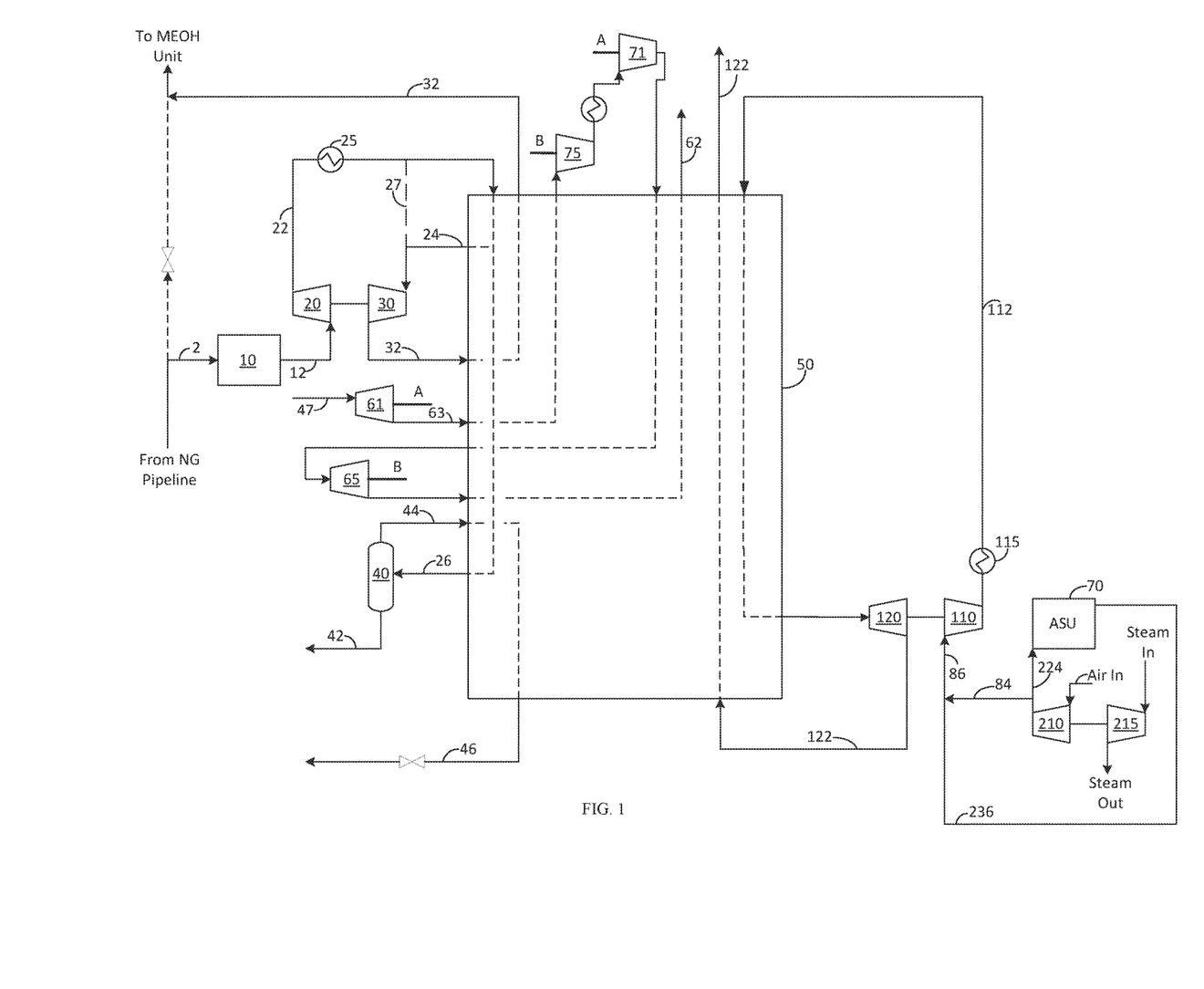
FIG. 1 shows an embodiment of the present invention.

Now turning to FIG. 1. Natural gas 2 is purified of carbon dioxide and water to form stream 12 before being compressed in compressor 20 to form pressurized natural gas 22. Pressurized natural gas 22 is then cooled by aftercooler 25 to remove heat of compression from compressor 20.

Figure 5:
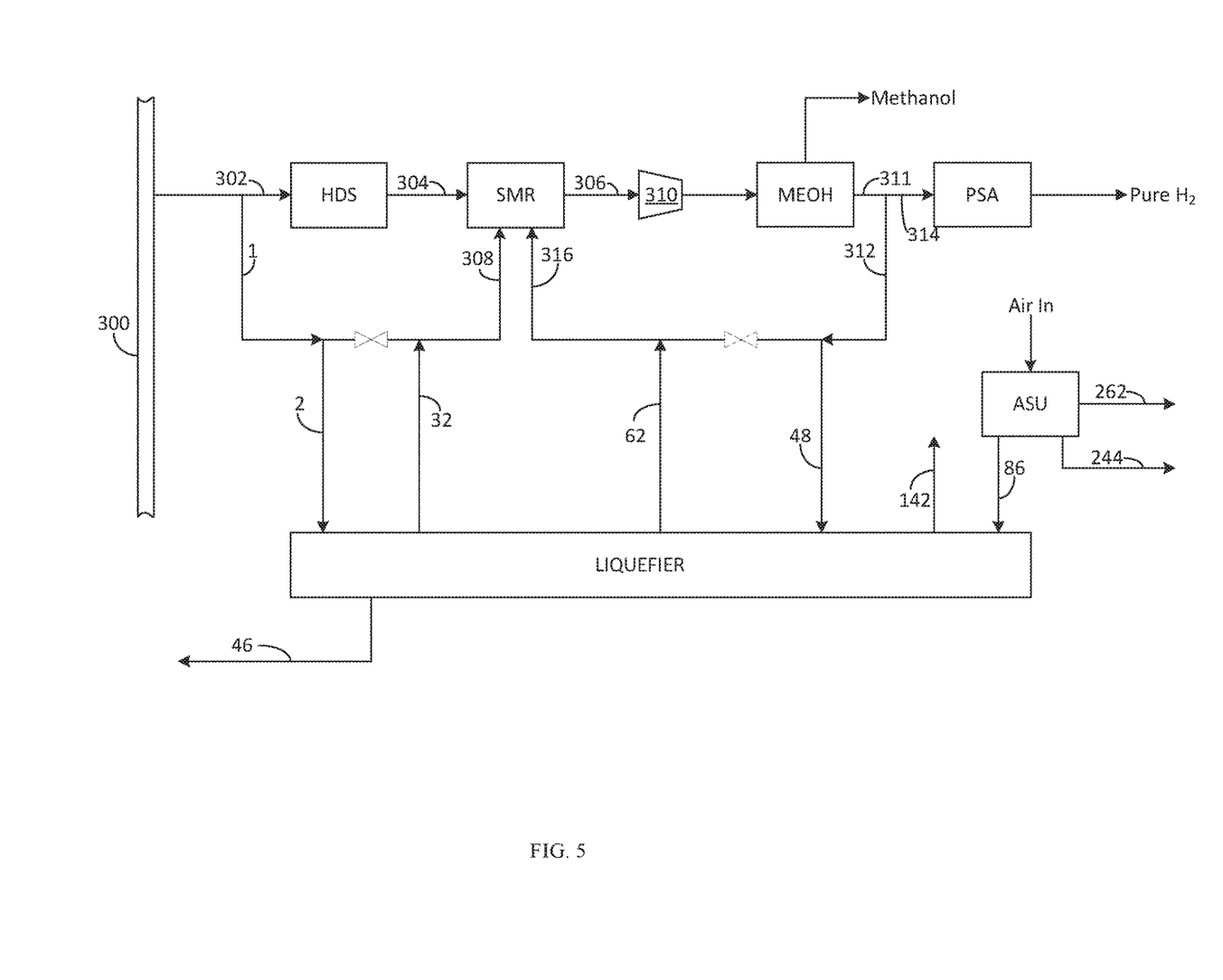
FIG. 5 shows an embodiment of an integrated methanol production facility with an ASU and liquefier in accordance with an embodiment of the present invention.

For the warm end refrigeration (i.e., cold temperatures that are still warm enough to prevent freezing of trace components in the natural gas and high pressure purge gas, which in some embodiments is considered to be temperatures warmer than about −100° C. to −140° C.), pressurized natural gas 22 is then cooled within heat exchanger 50, wherein a first portion of the pressurized natural gas 24 is withdrawn at a first intermediate point of the heat exchanger where it is expanded in turbine 30 to low pressure to form first expanded portion 32, before being warmed in heat exchanger 50 and subsequently sent to the methanol plant to be used as fuel (see lines 32 and 308 of FIG. 5). Alternatively, after exiting aftercooler 25, the pressurized natural gas may be sent directly to the inlet of turbine 30 via line 27 rather than cooling the gas in exchanger 50 for the purpose of limiting the temperature at the discharge of the turbine. Alternatively, cooler 25 may be reduced or removed to further warm stream 32.

First expanded portion 32 provides a first portion of the refrigeration used to cool and eventually liquefy the industrial gas, which in the embodiment shown is natural gas. The turbine 30 can drive a generator or booster to pre-boost the total natural gas feed as shown, or only the natural gas to be liquefied, or only the natural gas to be expanded, or to post-boost the natural gas which was expanded.

In the embodiment shown in FIG. 1, purge gas 48 can be expanded in first turbine 61. Following expansion, the expanded hydrogen rich purge gas 63 is warmed before being boosted in first booster 75 and second booster 71, which can be driven by turbines 65 and 61, respectively. The compressed purge stream is then partially re-cooled in the main exchanger, expanded again in a second set of turbines 65 and re-warmed in the main exchanger, thereby providing additional refrigeration to the industrial gas. The expanded purge gas 62 is then sent to the methanol plant for use as fuel. This arrangement provides increased refrigeration production by utilizing the higher pressure ratios of the purge gas letdown while at least partially offset by additional cycle complexity and capital cost.

Figure 2:
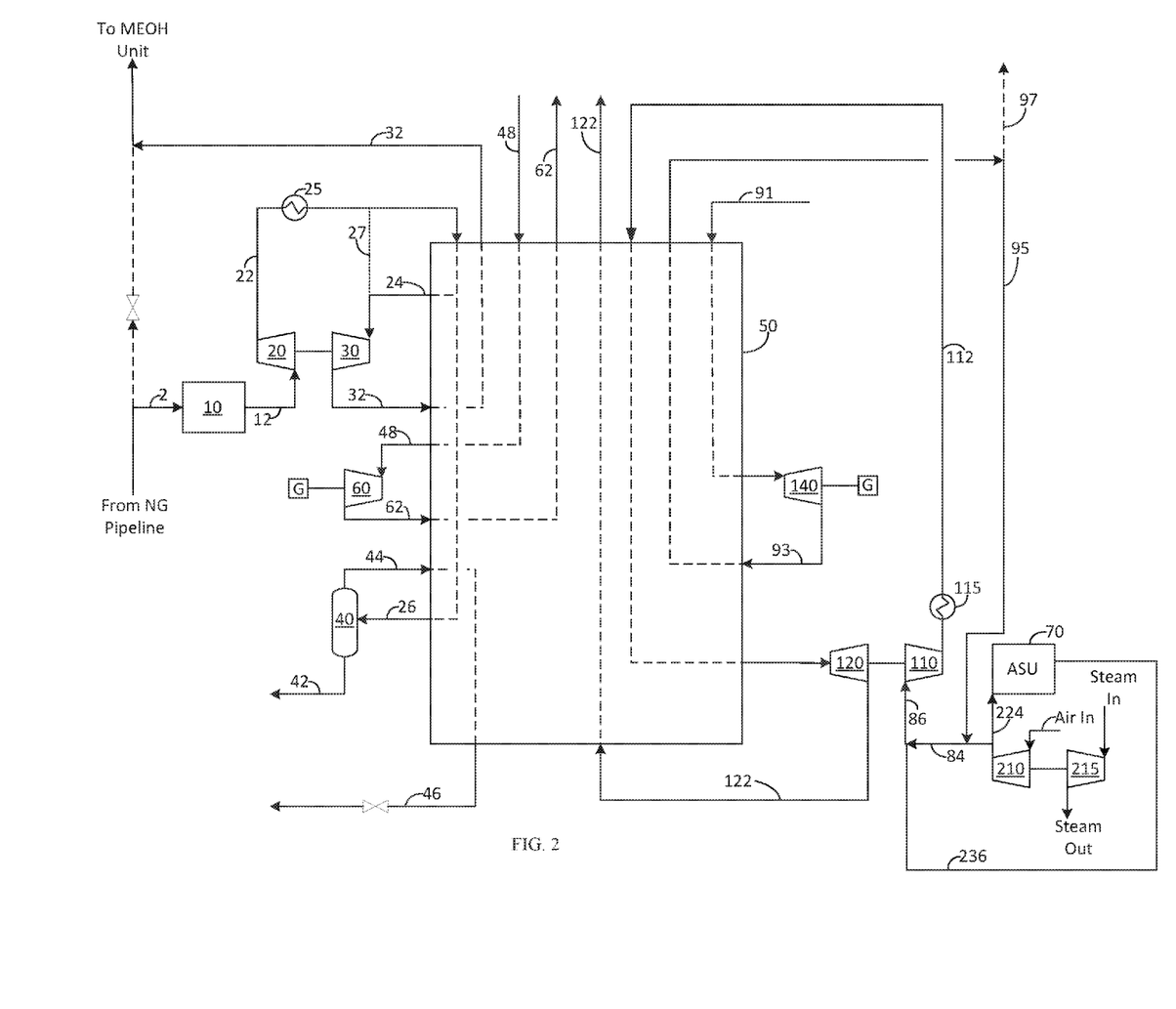
FIG. 2 shows a second embodiment of the present invention.
Figure 3:
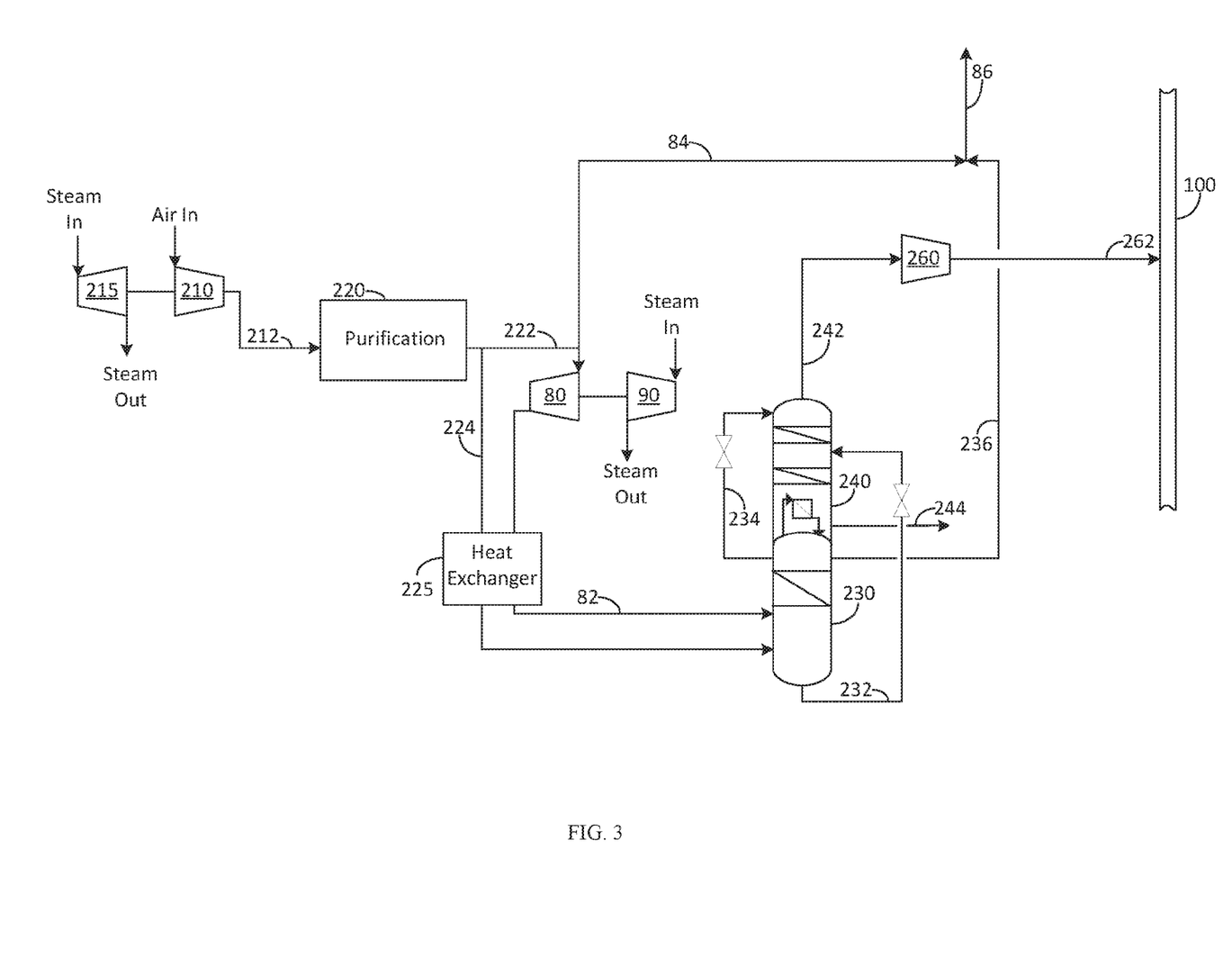
FIG. 3 shows an embodiment of the air separation unit and nitrogen pipeline in accordance with an embodiment of the present invention.

In the embodiment shown in FIG. 2, purge gas 48, which is a high pressure hydrogen rich stream (see 312 of FIG. 3) received from the methanol plant, can be partially cooled (e.g., the purge gas is removed from an intermediate section of the heat exchanger), expanded in second turbine 60 (or set of turbines arranged in series or parallel), which is linked to a generator G, to form expanded purge gas 62 before being warmed in the main exchanger, and sent back to the methanol plant as low pressure fuel (see 316 of FIG. 3). Expanded purge gas 62 provides a second portion of the refrigeration used to cool and eventually liquefy the natural gas.

Remaining with FIG. 2, the refrigeration can be supplemented by a supplemental high pressure nitrogen 91 sourced from a high pressure nitrogen source (e.g., a pipeline), which is preferably at a pressure of 15-100 bara. The supplemental high pressure nitrogen 91 is cooled in the main exchanger 50 and expanded in expander 140 to a pressure sufficient to mix with the ASU MAC air discharge pressure and the medium pressure nitrogen draw pressure (e.g., pressure of stream 236). In one embodiment, this high pressure turbine 140 drives a generator; however, those of ordinary skill in the art will recognized that it could also provide pre- or post-boost to the nitrogen stream.

Now returning to FIG. 1, in an optional embodiment, if second portion of the pressurized natural gas 26 (stream to be liquefied as product LNG) contains heavy hydrocarbons such as butane and heavier, it can be withdrawn at a second intermediate point of the heat exchanger and introduced to a liquid/gas separator or distillation column to remove heavy hydrocarbons 42, leaving a top gas 44 that is more concentrated in methane. Top gas 44 is reintroduced into the intermediate and/or cold end of heat exchanger 50, wherein it is further cooled and liquefied to form liquefied natural gas (LNG) 46.

Cold end refrigeration (i.e., temperatures colder than what can be achieved from the purge gas and natural gas expansion or colder than about −100° C. to −140° C.) can be provided by a boosted air stream 84, a nitrogen stream 236, and/or a nitrogen-air mixture 86. In the embodiment shown in FIG. 1, nitrogen-air mixture 86 is used. In the embodiment shown, nitrogen-air mixture 86 is at a medium pressure (e.g., approximately 4-7 bara) before being boosted by booster 110, cooled in aftercooler 115 to form high pressure air mixture, wherein it is partially cooled in heat exchanger 50, expanded in expander 120 to approximately the range of 1.1 to 2.0 bara to form expanded air mixture, and then warmed in heat exchanger 50. Expanded air mixture 122 provides a third portion of the refrigeration used to cool and eventually liquefy the natural gas. Following heat transfer, expanded air mixture 122 can be vented to the atmosphere, used as a dry gas to an evaporative cooling system, or recompressed.

In another embodiment, which is shown in FIG. 2, there may be a requirement for utility nitrogen at a pressure of 5 to 10 bara at the facility, which is typically supplied by a high pressure $N_2$ pipeline. In this embodiment, the discharge pressure of expander 140 may be adjusted slightly per the customer's demand pressure, such that a first portion 97 can be removed as product with the remainder 95 available for mixing with air 84 from MAC 210.

In another embodiment, heat exchanger 50 may be split into parallel trains such that there is little to no risk of cold refrigerant leaking and being in contact with the hydrogen rich purge gas, or natural gas streams. In this embodiment, the oxygen content in the cold refrigerant can be increased to that of the combustibility limits.

FIG. 3 provides a schematic representation of an air separation unit in accordance with an embodiment of the invention. Air is compressed in main air compressor (MAC) 210, which can be driven by a motor (not shown) or by steam turbine 215 if excess steam is available from a nearby source, such as the methanol unit, to produce compressed air 212. Compressed air 212 is then purified in purification unit 220 to remove components that will freeze at cryogenic temperatures (e.g., carbon dioxide and water). From there, compressed air 212 can be split into first portion 222, second portion 224, and third portion 84, wherein the second portion is cooled in ASU heat exchanger 225 and then introduced to the double distillation column for rectification therein. In certain embodiments, first portion 222 can be further compressed in booster air compressor (BAC) 80 before being cooled in the ASU heat exchanger 225 and then introduced into medium pressure column 230. Third portion of the compressed air stream 84 is sent to the liquefier as described in FIG. 1 or FIG. 2, either alone or combined with nitrogen stream 236 from medium pressure nitrogen stream 236 (e.g., the combination of air 84 and nitrogen 236 forms nitrogen-air mixture 86).

The double distillation column shown is a typical double distillation column in an air separation unit comprising lower pressure column 240, shared condenser/reboiler 241, and higher pressure column 230 (sometimes also referred to herein as medium pressure column). Bottoms liquid 232 rich in oxygen is expanded across a valve before being introduced into lower pressure column 240 for further separation. Nitrogen stream 234 is also introduced into lower pressure column 240 as reflux. Liquid oxygen stream 244 is produced at a bottom section of lower pressure column 240 as product or vaporized in ASU heat exchanger 225 for gaseous oxygen production (not shown). Low pressure nitrogen stream 242 is produced at the top of low pressure column 240, and medium pressure nitrogen stream 236 is produced at a top portion of higher pressure column 230.

In one embodiment, low pressure nitrogen stream 242 can be further compressed by compressor 260 to form high pressure nitrogen 262, which can then be introduced to nitrogen pipeline 100.

Figure 4:
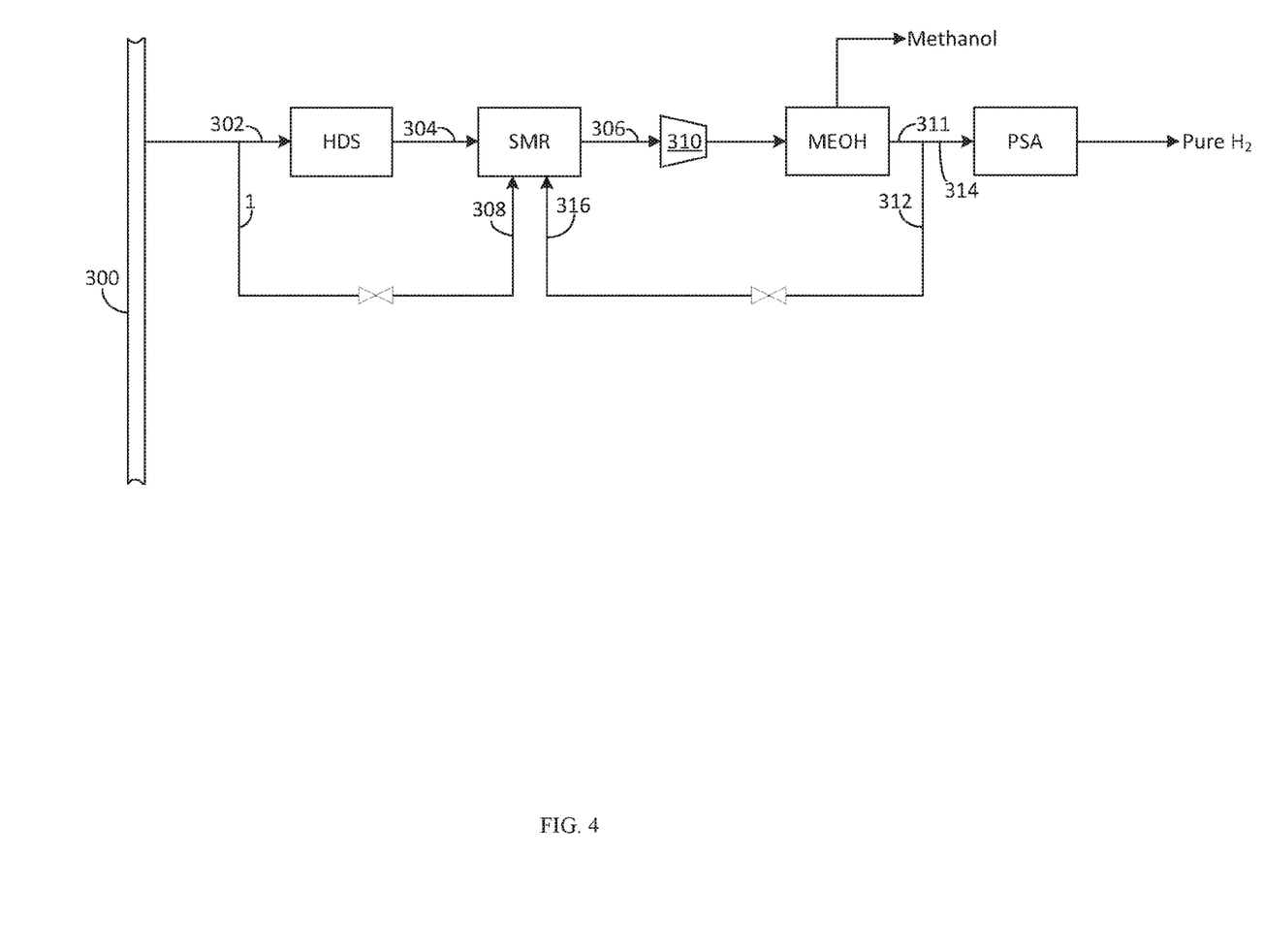
FIG. 4 shows an embodiment of a methanol production facility in accordance with an embodiment of the present invention.

FIG. 4 provides a schematic overview of a methanol plant 301. Natural gas is withdrawn from natural gas pipeline 300, with a first portion of the natural gas 302 being sent to a hydro-desulfurization (HDS) unit to remove sulfur to form a desulfurized natural gas 304. This stream is then sent to a steam methane reformer (SMR) under conditions effective for producing syngas 306, which is then pressurized in compressor 310 before being sent to the methanol production facility (MEOH) under conditions effective for producing methanol and a purge gas 311. A first portion of the purge gas 314 is then sent to a pressure swing adsorber (PSA) in order to recover purified hydrogen. In a typical methanol plant, second portion of the purge gas 312, which is at an increased pressure of only nominally less than that of the discharge pressure of compressor 310, is typically expanded across a valve to very low pressure (e.g., about atmospheric pressure) and then sent to the SMR for use as purge gas fuel 316. Similarly, it is typical to supplement this fuel by use of a second portion of the natural gas 1 for use as fuel to the SMR after expansion in a valve via line 308.

FIG. 5 provides a schematic overview of an integrated methanol plant, liquefier and ASU in accordance with an embodiment of the present invention. In embodiments of the present invention, instead of wasting the expansion energy of natural gas 1 and second portion of the purge gas 312 by expansion across a valve, natural gas 2 and purge gas 48 are sent to the liquefier, as described in FIG. 1 or FIG. 2, in order to provide a portion of the refrigeration used to cool and liquefy the natural gas.

Integration of the methanol plant, liquefier, and ASU provides significant energy savings compared to a standalone natural gas liquefier. In one embodiment, all of the refrigeration used for liquefaction of the gas stream is provided by the cooling energy provided from the expansion of the natural gas, purge gas and air gas from the ASU (or nitrogen pipeline), thereby providing liquefaction of the natural gas and/or nitrogen gas with minimal or no additional compression costs. Alternatively, for increased liquefaction, this liquefaction energy can be supplemented by one or more additional liquefaction energy sources such as a cycle compressor driven by electric, gas turbine, or steam turbine drive.

In the embodiment shown in FIG. 1, 274 mtd of LNG can be produced using between 92 and 163 kW/mt depending on if free steam is available to drive the main air compressor. In the embodiment of FIG. 2, approximately 428 mtd LNG can be produced for about 146 kW/mt if free steam is available to drive the air compressor and 223 kW/mt if free steam is not available. In comparison, a stand-alone LNG plant would produce that amount of LNG for about 660 kW/mt. Clearly, even without free steam, embodiments of the invention provide a significant operational savings.

As used herein, "purge gas stream" is process gas to be withdrawn from the pressurized synthesis process to remove impurities and inerts from the catalytic process. The purge gas from methanol plants typically contains between 50-80% hydrogen.

While the invention has been described in conjunction with specific embodiments thereof, it is evident that many alternatives, modifications, and variations will be apparent to those skilled in the art in light of the foregoing description. Accordingly, it is intended to embrace all such alternatives, modifications, and variations that fall within the spirit and broad scope of the appended claims. The present invention may suitably comprise, consist or consist essentially of the elements disclosed and may be practiced in the absence of an element not disclosed. Furthermore, language referring to order, such as first and second, should be understood in an exemplary sense and not in a limiting sense. For example, it can be recognized by those skilled in the art that certain steps or devices can be combined into a single step/device.

The singular forms "a", "an", and "the" include plural referents, unless the context clearly dictates otherwise. The terms about/approximately a particular value include that particular value plus or minus 10%, unless the context clearly dictates otherwise.

Optional or optionally means that the subsequently described event or circumstances may or may not occur. The description includes instances where the event or circumstance occurs and instances where it does not occur.

Ranges may be expressed herein as from about one particular value, and/or to about another particular value. When such a range is expressed, it is to be understood that another embodiment is from the one particular value and/or to the other particular value, along with all combinations within said range.

We claim:

1. A method for the liquefaction of an industrial gas selected from the group consisting of natural gas, nitrogen, hydrogen, and combinations thereof, the method comprising the steps of:
   a) withdrawing a natural gas stream from a natural gas pipeline;
   b) removing carbon dioxide and water from the natural gas stream to produce a purified natural gas stream;
   c) expanding a first portion of the purified natural gas stream to form an expanded natural gas stream and warming the expanded natural gas stream in a first portion of a heat exchanger against the industrial gas to form a warmed natural gas stream;
   d) sending the warmed natural gas stream to a methanol production facility under conditions effective for producing a methanol stream, a purified hydrogen stream, and a purge gas rich in hydrogen;
   e) expanding the purge gas rich in hydrogen to form an expanded purge gas and warming the expanded purge gas in a second portion of the heat exchanger against the industrial gas to form a warmed purge gas stream;
   f) sending the warmed purge gas stream to the methanol production facility for use as fuel; and
   g) expanding a pressurized air gas stream from or derived from an air separation unit (ASU) to form an expanded air gas stream and warming the expanded air gas stream in a third portion of the heat exchanger against the industrial gas to form a warmed air gas stream,
   wherein the industrial gas is liquefied during step g), wherein the industrial gas comprises a second portion of the purified natural gas stream.

2. The method as claimed in claim 1, wherein the air gas from or derived from an ASU is a gas stream selected from the group consisting of compressed and purified air from a main air compressor, a nitrogen stream from a medium pressure column, and combinations thereof.

3. The method as claimed in claim 1, wherein the industrial gas further comprises trace components having a freezing point temperature warmer than that of methane, wherein the first portion of the heat exchanger and the second portion of the heat exchanger are kept at temperatures warmer than the freezing point temperature of the trace components, and wherein the trace components are removed from the industrial gas prior to the industrial gas being cooled in the third portion of the heat exchanger.

4. The method as claimed in claim 1, wherein the third portion of cooling is provided at colder temperatures than both the first portion of cooling and the second portion of cooling.

5. A method for the liquefaction of an industrial gas, the method comprising the steps of:
  (a) providing a pressurized natural gas stream, a pressurized purge gas stream originating from a methanol plant, and a pressurized air gas stream comprising an air gas from an air separation unit (ASU), wherein the pressurized purge gas stream is comprised predominately of hydrogen, wherein the pressurized air gas stream has an oxygen concentration at or below that of atmospheric air;
  (b) expanding a first portion of the pressurized natural gas stream to produce an expanded natural gas stream, expanding the pressurized purge gas stream to produce an expanded purge gas stream, and expanding the pressurized air gas stream to produce an expanded air gas stream; and
  (c) liquefying the industrial gas in a liquefaction unit against the expanded natural gas stream, the expanded purge gas stream, and the expanded air gas stream to produce a liquefied industrial gas stream,
  wherein the industrial gas to be liquefied is selected from the group consisting of a second portion of the pressurized natural gas stream, a nitrogen gas stream from a nitrogen pipeline, a nitrogen gas stream from the ASU, hydrogen and combinations thereof.

6. The method as claimed in claim 5, wherein the air gas from an ASU is a gas stream selected from the group consisting of compressed and purified air from a main air compressor, a nitrogen stream originating from a medium pressure column of the ASU, and combinations thereof, wherein the air gas from the ASU is at a pressure between 4 and 40 bara.

7. The method as claimed in claim 5, wherein the pressurized natural gas stream comprises methane and trace components, wherein the trace components have freezing point temperatures warmer than that of methane.

8. The method as claimed in claim 7, wherein the trace components have a freezing point temperature warmer than about −140° C.

9. The method as claimed in claim 7, wherein in steps (b) and (c):
  the pressurized natural gas stream provides a first portion of cooling to the industrial gas,
  the pressurized purge gas stream provides a second portion of cooling to the industrial gas, and
  the pressurized air gas stream provides a third portion of cooling to the industrial gas, wherein the third portion of the cooling is at a temperature that is colder than the first portion of the cooling and the second portion of the cooling.

10. The method as claimed in claim 5, wherein the pressurized air gas stream further comprises nitrogen gas from a nitrogen pipeline.

11. The method as claimed in claim 5, wherein the air gas of the pressurized air gas stream is withdrawn at a location downstream a main air compressor (MAC) of the ASU at or slightly below an outlet pressure of the MAC.

12. The method as claimed in claim 11, wherein the flow of the air gas of the pressurized air gas stream withdrawn at a location downstream of the MAC and provided in step (a) has an increased flow during periods wherein there is no repressurization step taking place within a front end purification unit of the ASU.

13. The method as claimed in claim 11, wherein the flow of the air gas of the pressurized air gas stream withdrawn from the outlet of the MAC and provided in step (a) accounts for less than about 20% of the total volumetric flow of air coming from the outlet of the MAC.

14. The method as claimed in claim 11, wherein the flow of the air gas stream of the pressurized air gas stream withdrawn from the outlet of the MAC and provided in step (a) accounts for less than about 5% of the total volumetric flow of air coming from the outlet of the MAC.

15. The method as claimed in claim 5, wherein the three different expansions in step (b) are performed in at least three separate turbines.

16. A method for the liquefaction of an industrial gas selected from the group consisting of nitrogen, natural gas, hydrogen and combinations thereof, the method comprising the steps of:
  a) withdrawing a natural gas stream from a natural gas pipeline;
  b) sending a first portion of the natural gas stream to a methanol production facility under conditions effective for producing a methanol stream, a purified hydrogen stream, and a purge gas rich in hydrogen;
  c) expanding a second portion of the natural gas stream to form an expanded natural gas stream;
  d) expanding the purge gas rich in hydrogen from step b) to form an expanded hydrogen stream;
  e) expanding a pressurized air gas stream from or derived from an air separation unit (ASU) to form an expanded air gas stream, wherein the air gas from or derived from an ASU is a gas stream selected from the group consisting of compressed and purified air from a main air compressor (MAC), a nitrogen stream from a medium pressure column, and combinations thereof;
  f) cooling the industrial gas in a heat exchanger against the expanded natural gas stream and the expanded hydrogen stream; and
  g) further cooling and liquefying the industrial gas in the heat exchanger against the expanded air gas stream to produce a liquefied industrial gas.

17. The method as claimed in claim 16, wherein the third portion of cooling is provided at colder temperatures than both the first portion of cooling and the second portion of cooling.

18. The method as claimed in claim 16, wherein the third portion of the natural gas stream is cooled to a temperature warmer than about −140° C. in step f).

19. The method as claimed in claim 16, wherein the third portion of the natural gas stream is cooled to a temperature between −140° C. to −165° C. in step g).

* * * * *